(12) United States Patent
Hanna

(10) Patent No.: US 11,000,617 B1
(45) Date of Patent: May 11, 2021

(54) SAFETY MEDIA FOR WAX MELTS

(71) Applicant: Burton Hanna, Fayetteville, AR (US)

(72) Inventor: Burton Hanna, Fayetteville, AR (US)

( * ) Notice: Subject to any disclaimer, the term of this patent is extended or adjusted under 35 U.S.C. 154(b) by 0 days.

(21) Appl. No.: 16/739,362

(22) Filed: Jan. 10, 2020

Related U.S. Application Data

(60) Provisional application No. 62/790,849, filed on Jan. 10, 2019.

(51) Int. Cl.
| | | |
|---|---|---|
| *A61L 9/04* | (2006.01) | |
| *C11D 3/50* | (2006.01) | |
| *A61K 8/00* | (2006.01) | |
| *A61K 8/18* | (2006.01) | |
| *A61L 9/012* | (2006.01) | |
| *A61L 9/03* | (2006.01) | |

(52) U.S. Cl.
CPC ............ *A61L 9/012* (2013.01); *A61L 9/035* (2013.01); *A61L 2209/13* (2013.01)

(58) Field of Classification Search
CPC .. A61K 8/00; A61K 8/18; A61Q 13/00; A61L 9/04; C11D 3/50
USPC .......................................... 512/4, 1
See application file for complete search history.

(56) References Cited

U.S. PATENT DOCUMENTS

| | | | | |
|---|---|---|---|---|
| 3,160,596 A * | 12/1964 | Spencer | ................. | C08J 9/0061 521/65 |
| 3,169,596 A | 2/1965 | Wright | ................. | 180/7 |
| 7,067,772 B2 | 6/2006 | Tanner et al. | ................. | 219/445.1 |
| 7,612,029 B2 * | 11/2009 | Foland | ................. | C11D 17/049 424/443 |
| 7,699,603 B2 | 4/2010 | Furner et al. | ................. | 431/292 |
| 2015/0173353 A1 * | 6/2015 | Zlotnik | ................. | A01N 27/00 424/409 |

OTHER PUBLICATIONS

Savannah, https://www.inspiredbysavannah.com/2017/11/holiday-gift-guide-2017-happy-wax.html, 2017 (Year: 2017).*
Yankee Candle Tart Wax melt, https://yankeecandle.com/browse/wax-rnelts/tarts-wax-melts/_/N-8eg, Aug. 12, 2014 (Year: 2014).*
Yankee Candle Tart Wax melt Wayback report, Aug. 24, 2014 (Year: 2014).*
John Mark Candles, www.johnmarkcandles.com/candle-cubes-1/, 2016 (Year: 2016).*
John Mark candles Wayback report, Apr. 12, 2016 (Year: 2016).*

* cited by examiner

*Primary Examiner* — Jessica Whiteley
(74) *Attorney, Agent, or Firm* — Keisling & Pieper PLC; Trent C. Keisling; David B. Pieper

(57) ABSTRACT

The invention includes an improved wax melt in a foam safety media of melamine for subsequent melting in a conventional warmer or other candle melting device. The melts release their fragrance when heated conventionally but remain associated with the foam safety media during use to be substantially spill-proof. The melts are produced by piping heated liquid wax with fragrance and other desirable components into a container that dispenses discrete quantities onto a melamine foam safety media on a moving conveyor for cooling and hardening and subsequent packaging into discrete wax melts in a melamine foam safety media.

7 Claims, 6 Drawing Sheets

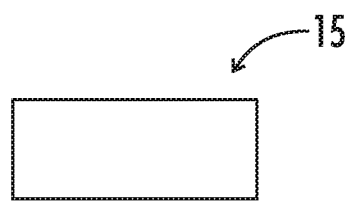
*FIG. 6*
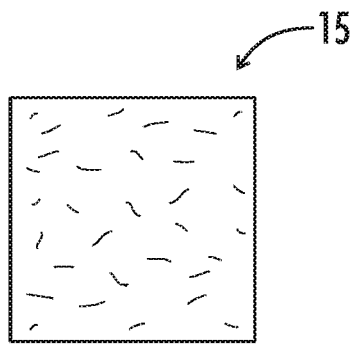 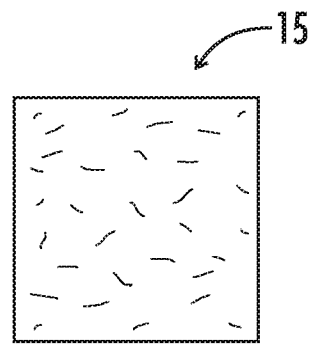
*FIG. 7*      *FIG. 8*

SAFETY MEDIA FOR WAX MELTS

CROSS-REFERENCE TO RELATED APPLICATIONS

This application claims priority to and is a continuation-in-part of provisional application Ser. No. 62/790,849 filed Jan. 10, 2019.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The invention pertains to improvements in candles and more particularly to those types of candles employed with plate warmers that melt the candle wax to emit the fragrance therefrom. Known art can be found in U.S. Class 510, subclass 295 and in U.S. Class 219, subclass 445.1 and in Class 219, subclass 292 and in other classes and subclasses.

2. Description of the Known Art

Those skilled in the art will appreciate that it is often desirable to dispense fragrances from candles without actually burning the candle. Devices such as candle warmers and plate warmers and the like have been developed to melt candles without using a flame, typically by an electrically powered burner that simply melts the candle. Other types of waxes without wicks and with fragrances may also be used with these systems and these are often called wax melts. While conventional candles may be used with such systems, they do not work as well as smaller wax objects such as cubes or the like that are specifically made for such warmers. The wax objects are typically sized to melt completely and uniformly on the warmer and have a high concentration of fragrance per volume of the carrier (i.e. the wax). A problem with these wax melts is that they can be easily spilled, which can damage furniture or persons. Thus, a spill proof media for wax melts used for fragrance diffusing in electric and tea light wa titers is desirable. It is also advantageous that the media be recyclable such that it can be recharged with fragrance and subsequently reused as desirable.

Known art which may be relevant to the present invention includes the following patents with their abstracts, the teachings of which are incorporated by reference.

U.S. Pat. No. 7,612,029, issued to Foland, et al., on Nov. 3, 2009, entitled Controlled release using gels in a melamine foam is for a substrate comprising a nonwoven layer containing an ionically crosslinked polymer can be used to control the release of active ingredients. The substrate can be a melamine foam and contain a surfactant and an alginate polymer crosslinked with calcium. This is not for a wax melt but rather for cleaning compositions.

U.S. Pat. No. 3,169,596, issued to Spencer, on Dec. 6, 1964, entitled Wax containing Melamine-Formaldehyde foam and process of making same, is for rigid formaldehyde foams with reduced water vapor permeability. These foams have wax rigidly incorporated into their structure in minor amounts (i.e. less than 10% by weight) when cured and they are not subsequently separated.

U.S. Pat. No. 7,067,772, issued to Tanner, et al., on Jun. 27, 2006, entitled Candle warming apparatus, is for a hot plate warming apparatus adapted to warm a candle or other object resting thereon, as well as to provide illumination that simulates the effects of a lighted burning candle. The apparatus may include an adjustable cord apparatus, a light source, and/or a component enabling attachment of other peripheral components. The light source is positioned proximal to the hot plate for providing illumination to an object or substance resting on the hot plate or housing. The adjustable cord apparatus provides electricity to the warming apparatus while allowing a user to alter the length of the cord that is extending from the warming apparatus. The apparatus also comprises a blower to facilitate heating of a candle placed thereon, as well as to cause scented particles emanating from the melted wax or wax-like substance to be better dispersed or dissipated into the surrounding air. The attachment component permits additional peripheral components or materials to be removably coupled to the warming apparatus, such as interchangeable face plates, covers, craft objects, or module objects.

U.S. Pat. No. 7,699,603, issued Furner, et al., on Apr. 20, 2010, entitled Multisensory candle assembly, is for a candle assembly that includes a support base with a melting plate upon which a meltable solid fuel rests and a wick holder to hold a wick and engage the meltable solid fuel, and a control unit having at least one electrical component to control at least one of a sound emitting system or a light emitting system. In another aspect, a candle assembly includes a sensor configured to detect the presence of a flame disposed on the wick and controls the at least one of the sound emitting system or the light emitting system, and a lock and key mechanism. Another candle assembly includes a replaceable container to hold a meltable fuel element with a wick and a first mating surface and a control unit having at least one electrical component to control at least one of a sound emitting system or a light emitting system. In another aspect, the control unit has a second mating surface complimentary to the first mating surface and a sensor configured to detect the presence of a flame disposed on a wick. The sensor controls the at least one of the sound emitting system or the light emitting system, and the first mating surface is configured to mate with the second mating surface in a pre-selected spatial orientation to permit the sensor to detect the presence of a flame.

Also, commercially available equipment and components may be relevant, including commercial plate warmers or candle warmers or the like. Such equipment may be used in implementing an exemplary embodiment in accordance with the present invention.

None of these references, either singly or in combination, disclose or suggest the present invention. It is desirable to have an improved wax melt safety media that prevents spills of molten wax and a process for making wax melts with the safety media to address the perceived shortcomings of the known art.

While it is evident from past attempts that devices for melting candles and wax are known, candles or wax particularly adapted for melting plates and similar devices where the wax is safely contained when molten have not been used but are desirable. It is also desirable to provide small wax melts in the safety media that are prepackaged into single serving containers.

SUMMARY OF THE INVENTION

The present invention addresses the perceived needs in the known art discussed above. In this regard, the present invention substantially fulfills this need. The new wax objects of the present invention provide small wax melts in a safety media that may be advantageously employed with conventional wax warmers and/or candle melting devices. The media may also be recharged and reused as desirable.

In one exemplary embodiment in accordance with the present invention an improved wax object is provided that is contained within a melamine foam safety media and that is highly fragranced.

In another exemplary embodiment in accordance with the present invention, an improved fragrance dispensing system that uses small, substantially uniform wax carriers in a safety media with discrete fragrances is provided.

It is an object of the present invention to provide an improved wax object for melting. It is another object of the present invention to provide a safety media for wax melts that houses sufficient fragrance for a single use.

Another object is to provide wax melts in a foam that may be easily used with and adapted to existing melt devices.

These and other objects and advantages of the present invention, along with features of novelty appurtenant thereto, will appear or become apparent by reviewing the following detailed description of the invention in conjunction with the appended drawings.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views:

FIG. 6 is an elevational view photograph showing a side thereof;

FIG. 7 is a top plan view photograph thereof;

FIG. 8 is a bottom plan view photograph thereof;

Figure 10:
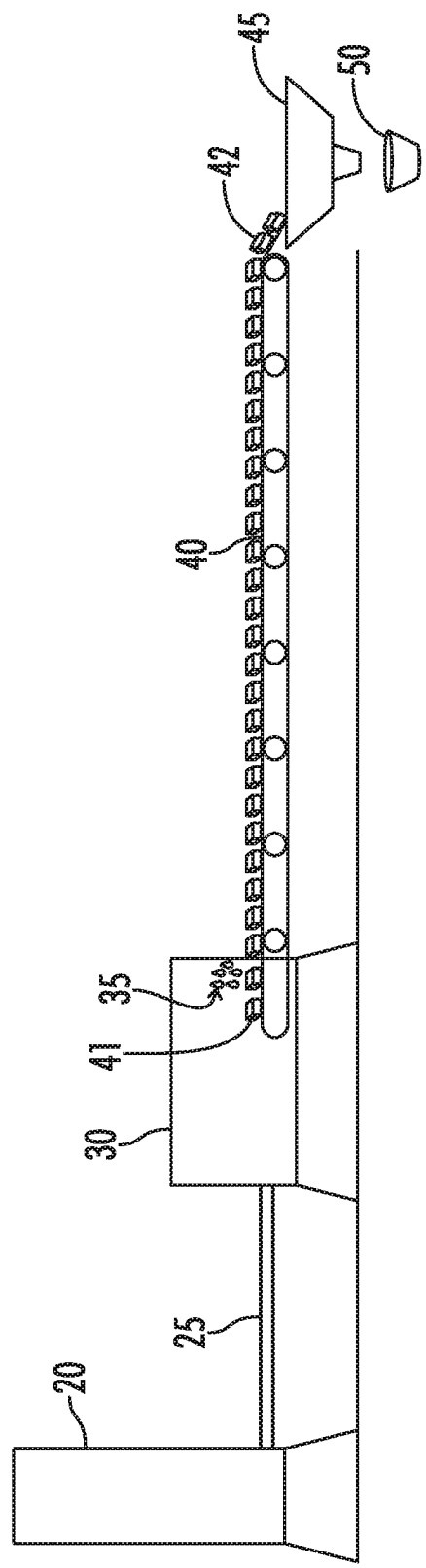

and,

FIG. 10 is a process diagram showing another process for wax melts in a foam safety media.

DETAILED DESCRIPTION OF THE INVENTION

The present invention addresses the perceived needs in the known art discussed above. In this regard, the present invention substantially fulfills this need.

Figure 1:
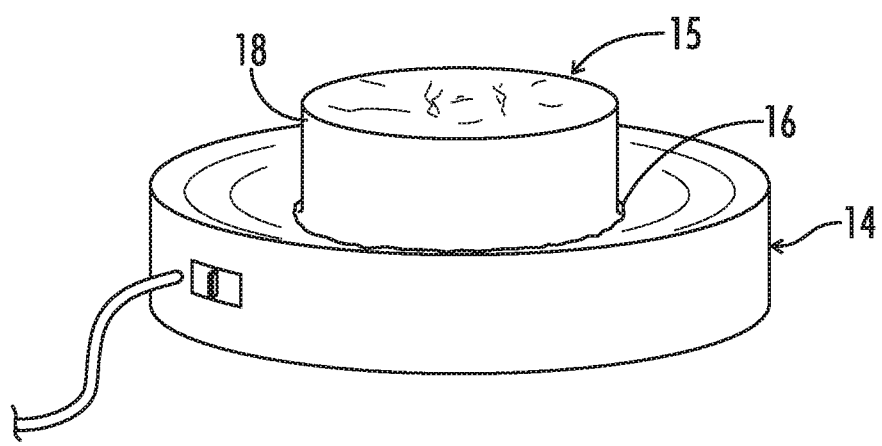
FIG. 1 is a perspective view photograph showing one exemplary embodiment of the wax melt in a foam safety media in accordance with the present invention.
Figure 2:
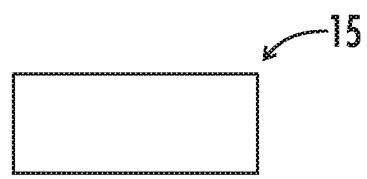
FIG. 2 is a side elevational view photograph thereof.
Figure 3:
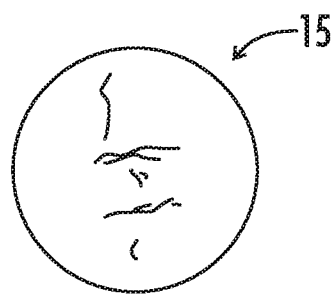
FIG. 3 is a top plan view photograph thereof.
Figure 4:
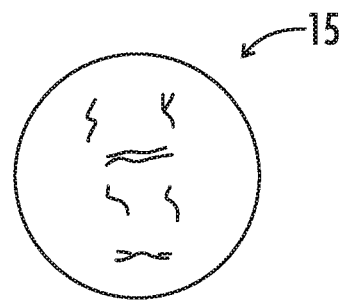
FIG. 4 is a bottom plan view photograph thereof.
Figure 5:
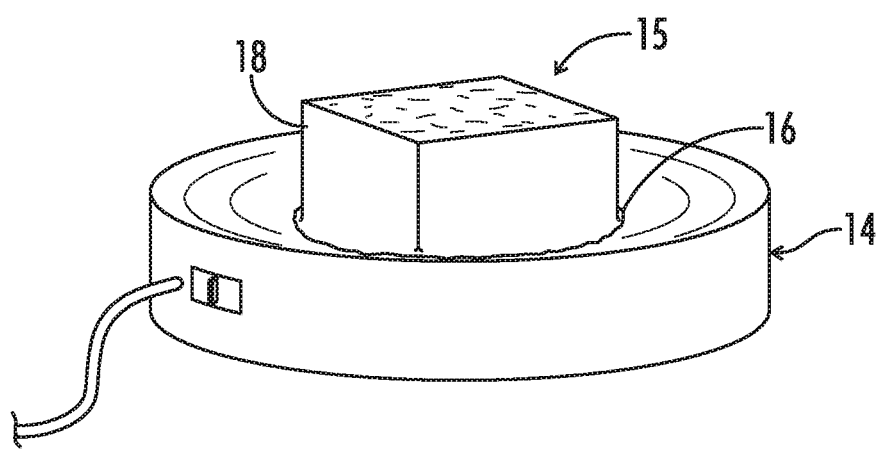
FIG. 5 is a perspective view photograph of another exemplary embodiment of a single serve wax melt in a foam safety media in accordance with the present invention.

The invention includes an improved wax melt in a foam safety media of melamine for subsequent melting in a conventional warmer or other candle melting device 14 (FIGS. 1 and 5). The melt bodies 20 release their fragrance when heated conventionally but remain associated with the foam safety media during use to be substantially spill-proof (FIGS. 1-8). The melts are produced by piping heated liquid wax with fragrance and other desirable components into a container that dispenses discrete quantities onto a melamine foam safety media on a moving conveyor for cooling and hardening and subsequent packaging into discrete wax melts in a melamine foam safety media body.

The wax to fragrance weight ratios and vary widely from 0% wax (i.e. 100% fragrance) to as much as 99% wax and only 1% fragrance. Experimentation has shown that wax and fragrance combinations that outweigh the melamine foam work acceptably with respect to fragrance "throw" and lifespan but for some uses lesser amounts may be more suited.

The main consideration is that the amount of foam is sufficient to absorb all of the molten wax and fragrance when cooled to room temperature. These combinations also do not leak wax when warmed slightly but when heated in a conventional wax melter to above 120 degrees Fahrenheit a small wax pool 16 forms around the foam body perimeter 18 but the pool 16 remains associated with the foam 20 and if the melter is displaced (i.e. knocked over or otherwise upset), the pool 16 is quickly reabsorbed by the foam body 20 so that very little if any wax is spilled as a result of the displacement.

The wax melt is substantially housed within the foam until it is heated. The foam body 15 may vary in thickness and physical size, but disc shaped bodies from one-eighth of an inch to around 1 inch in thickness have worked well Also, cube-shaped bodies have worked well too (shown in FIGS. 1-8).

In another exemplary embodiment, the invention includes an improved wax melt on a foam safety media that may be advantageously packaged with several other similarly shaped wax melts in single serving quantities for subsequent melting in a conventional warmer or other candle melting device. The melts are produced by piping heated liquid wax with fragrance and other desirable components into a container that dispenses discrete quantities onto a melamine safety foam cube (e.g. cubic in shape) on a moving conveyor for cooling and hardening and then packaging the cooled and formed melts. The melts are used by melting in a simmering pot or melt plate to disperse the fragrance encapsulated in the wax.

More than one fragrance may be combined to produce pleasing aromas as well. The reason of this is so that the manufacturer can mix and match different fragrances within the safety media body itself. For instance a hazelnut and vanilla could be combined to create a toffee smell, or any other combination of color and fragrance as desirable.

Figure 9:
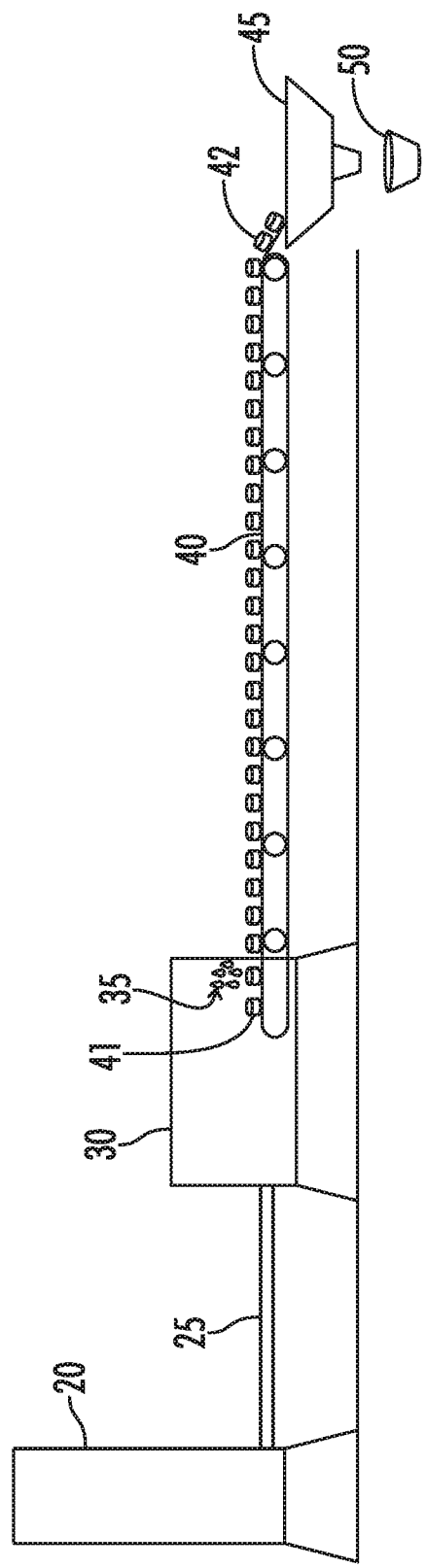
FIG. 9 is a process diagram showing a process for wax melts in a foam safety media.

To produce the melts, heated molten wax with other desirable components is combined with sufficient liquid fragrance to produce a liquid with 10-25% fragrance (FIGS. 9-10). The resultant liquid is mixed thoroughly in tank 20 and then piped via line 25 to dispenser 30. Dispenser 30 can be a conventional wax dispenser. The dispenser 30 places individual drops 35 onto a conveyor 40 on melamine foam safety media discs 41 (again a conventional conveyor available as above) where they cool and harden into individual melts 42 as the drops move along the conveyor 40 (e.g. travel distance of approximately 70 to 100 feet) to a collection bin 45. After the hardened melts 42 are collected and package conventionally. In another embodiment, the wax melts 42 are physically smaller and cube shaped and normally a sufficient quantity for a single serving (i.e. between 1/2 to 1 ounce of melts), and multiple cubes are placed into a package 50.

Other shapes and packaging configures are possible as well and so are varying wax and fragrance concentrations and contemplated by and within the scope of the present invention.

In describing a preferred embodiment of the invention illustrated in the drawings, specific teiminology has been used for the sake of clarity. However, the invention is not intended to be limited to the specific terms selected, and it is to be understood that each specific term includes all technical equivalents which operate in a similar manner to accomplish a similar purpose.

What is claimed is:

1. A wax melt comprising a heatable foam safety media of melamine having a porous body housing a charge of heatable mineral oil combined with a volatile fragrance, where the mineral oil and fragrance are substantially evenly dispersed throughout the body of the safety media and form a solid below about one hundred twenty degrees Fahrenheit but the mineral oil melts above about one hundred twenty degrees while remaining in and around the body but releasing the fragrance therefrom.

2. The wax melt of claim 1 where the body is a disc.

3. The wax melt of claim 1 where the body is a cube.

4. The wax melt of claim 1 wherein the body at least one eighth in an inch thick.

5. The wax melt of claim 1 wherein the body is less than one inch thick.

6. The wax melt of claim 1 wherein the melt further comprises multiple scents in a single melt.

7. The wax melt of claim 1 wherein the melt is packaged with multiple shaped melts with differing scents that enable a user to create unique scent combinations by melting multiple melts simultaneously.

* * * * *